(12) United States Patent
Akagane

(10) Patent No.: US 9,289,629 B2
(45) Date of Patent: Mar. 22, 2016

(54) ULTRASONIC PROBE AND MANUFACTURING METHOD OF ULTRASONIC PROBE

(71) Applicant: Olympus Corporation, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/300,780

(22) Filed: Jun. 10, 2014

(65) Prior Publication Data

US 2014/0358043 A1 Dec. 4, 2014

Related U.S. Application Data

(63) Continuation of application No. PCT/JP2013/065263, filed on May 31, 2013.

(60) Provisional application No. 61/680,534, filed on Aug. 7, 2012.

(51) Int. Cl.
*A61B 8/00* (2006.01)
*A61N 7/00* (2006.01)
(Continued)

(52) U.S. Cl.
CPC .......... *A61N 7/00* (2013.01); *A61B 17/320068* (2013.01); *A61B 2017/00526* (2013.01); *A61B 2017/320072* (2013.01);
(Continued)

(58) Field of Classification Search
CPC ...... A61B 8/00; A61B 2017/306; A61N 7/00; A61N 2007/0078
See application file for complete search history.

(56) References Cited

U.S. PATENT DOCUMENTS

| 5,047,043 | A | 9/1991 | Kubota et al. |
| 6,458,143 | B1 | 10/2002 | Sugai |
| 2001/0027325 | A1 | 10/2001 | Beaupre |

(Continued)

FOREIGN PATENT DOCUMENTS

| JP | A-62-211054 | 9/1987 |
| JP | A-63-305856 | 12/1988 |

(Continued)

OTHER PUBLICATIONS

Feb. 10, 2015 International Preliminary Report on Patentability issued in International Application No. PCT/JP2013/065263.

(Continued)

*Primary Examiner* — Joel Lamprecht
(74) *Attorney, Agent, or Firm* — Oliff PLC

(57) ABSTRACT

An ultrasonic probe transmits vibration along longitudinal axis from the proximal toward the distal end, including: first area including proximal and distal end portions, a center axis parallel to the longitudinal axis, the first area having a vibration antinode position at the distal end, wherein maximum distance from the center axis to an outer peripheral surface in radial direction orthogonal to the center axis is a first distance; a treatment section located on a distal end side's barycenter position displaced from the center axis; a second area located between the first area and treatment section continuous with the distal end of the first area and gravity center axis parallel to the center axis to pass through the barycenter, wherein maximum distance from the center axis to the outer surface in the radial direction orthogonal to the center axis is a second distance equal to or shorter than the first distance.

15 Claims, 13 Drawing Sheets

(51) Int. Cl.
*A61B 17/32* (2006.01)
*A61B 17/00* (2006.01)

(52) U.S. Cl.
CPC .............. *A61B 2017/320076* (2013.01); *A61B 2017/320088* (2013.01); *Y10T 29/49005* (2015.01)

(56) References Cited

U.S. PATENT DOCUMENTS

2009/0270891 A1* 10/2009 Beaupre .................. 606/169
2011/0040212 A1   2/2011 Dietz et al.

FOREIGN PATENT DOCUMENTS

| | | |
|---|---|---|
| JP | A-2000-041991 | 2/2000 |
| JP | A-2001-104326 | 4/2001 |
| WO | WO 2007/011813 A2 | 1/2007 |
| WO | WO 2010/047395 A1 | 4/2010 |
| WO | WO 2011/020097 A2 | 2/2011 |

OTHER PUBLICATIONS

Jun. 25, 2013 International Search Report issued in International Application No. PCT/JP2013/065263 (with translation).
Jul. 1, 2014 Japanese Office Action issued in Japanese Application No. 2014-523127 (with translation).

* cited by examiner

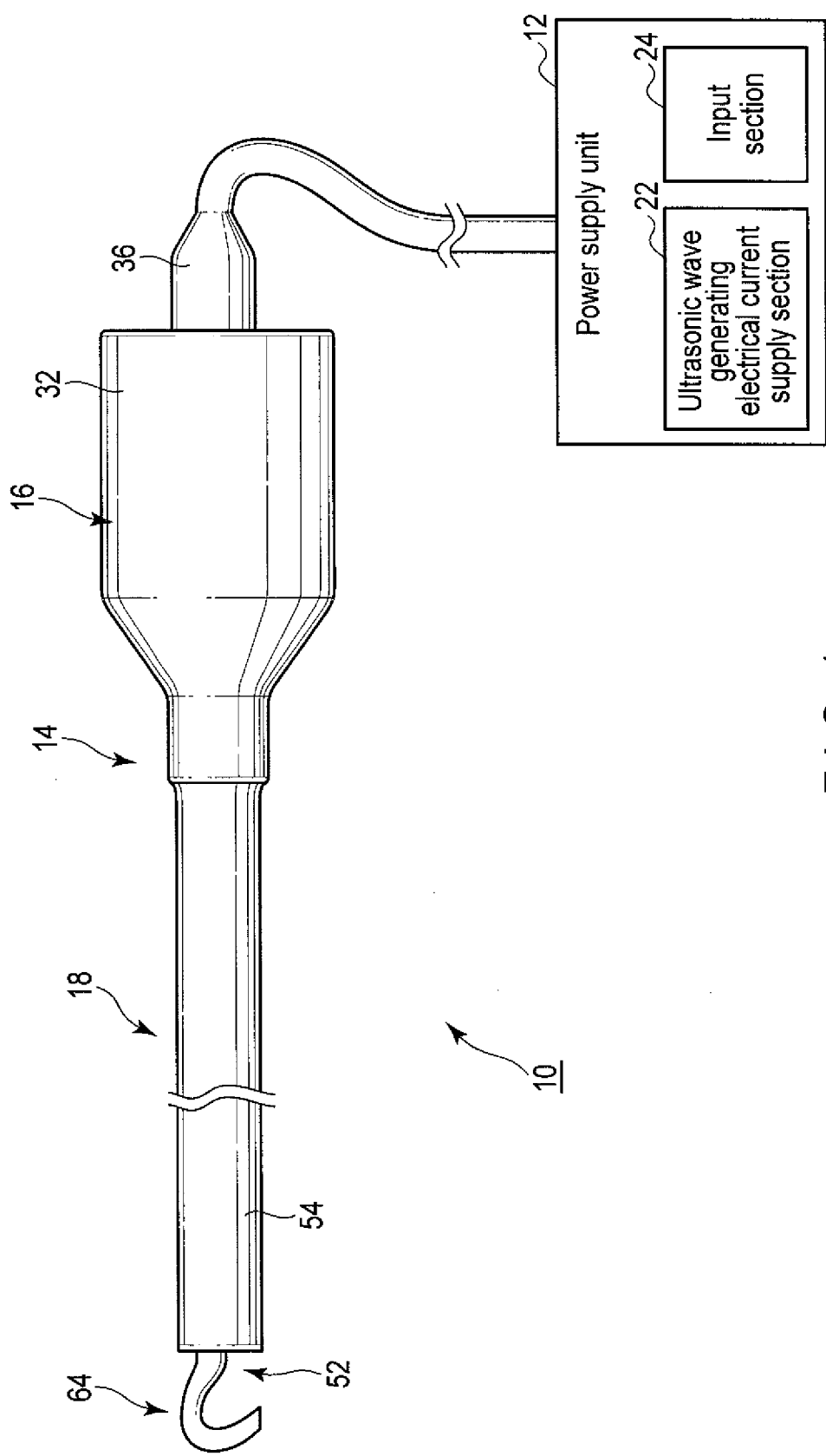
F I G. 1

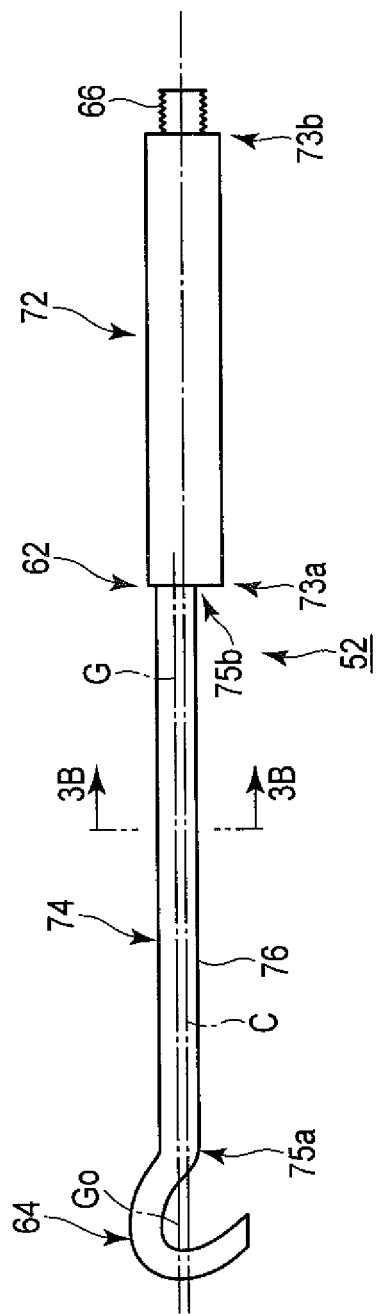

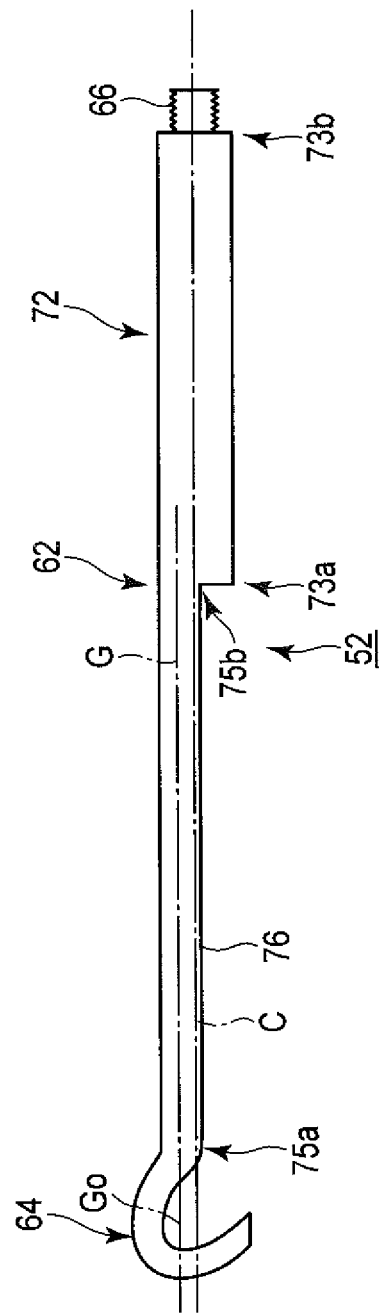
F I G. 3C

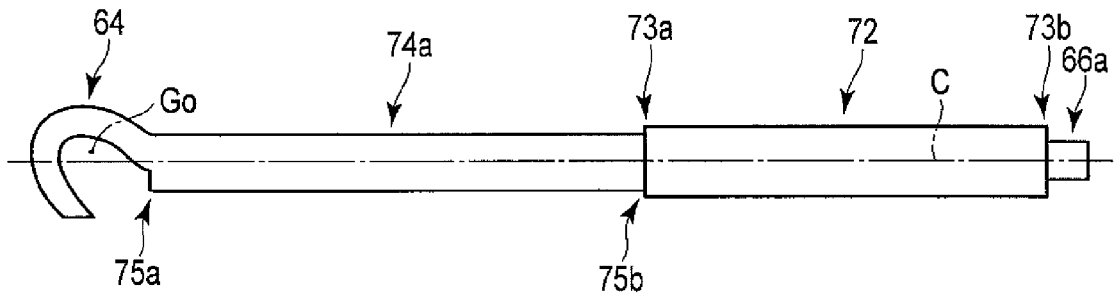
F I G. 4D
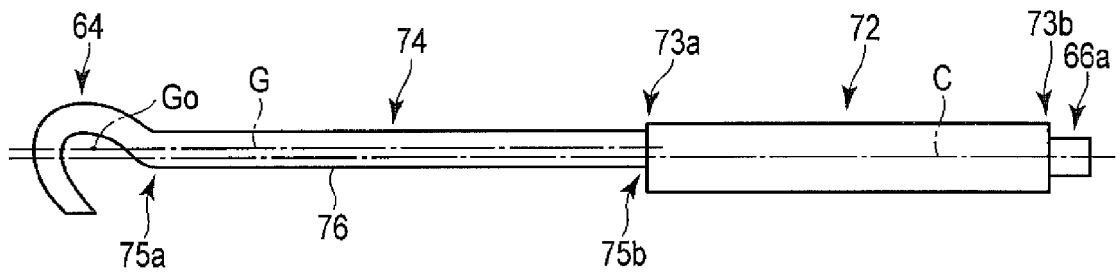
F I G. 4E
F I G. 5A

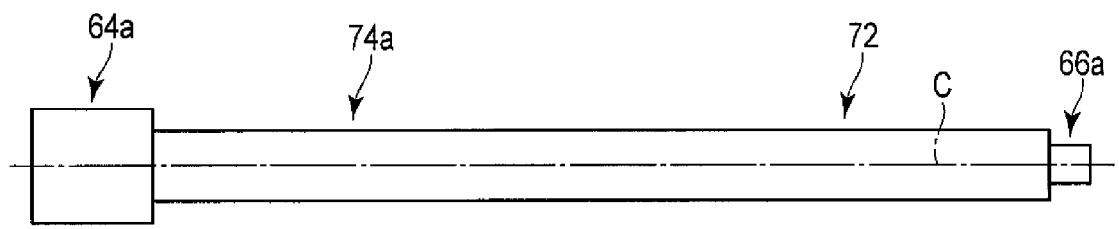
F I G. 5B
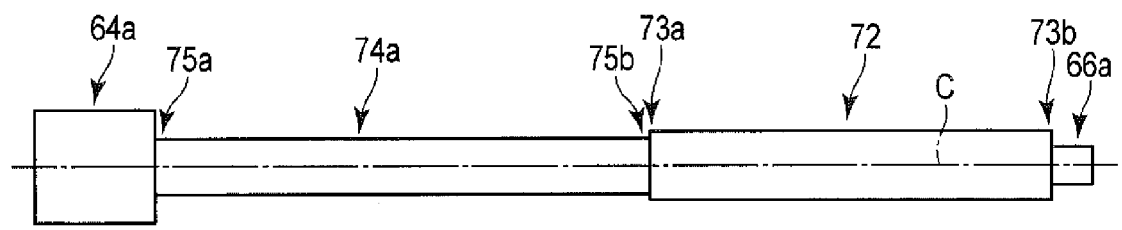
F I G. 5C
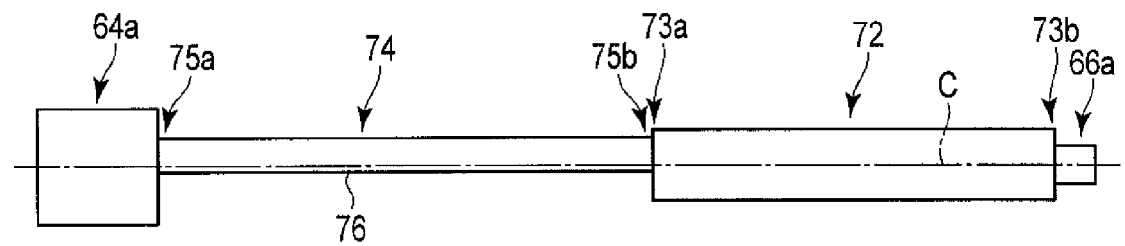
F I G. 5D

ULTRASONIC PROBE AND MANUFACTURING METHOD OF ULTRASONIC PROBE

CROSS-REFERENCE TO RELATED APPLICATIONS

This application is a Continuation Application of PCT Application No. PCT/JP2013/65263, filed May 31, 2013 and based upon and claiming the benefit of priority from U.S. Provisional Application No. 61/680,534, filed Aug. 7, 2012, the entire contents of all of which are incorporated herein by reference.

BACKGROUND OF THE INVENTION

1. Field of the Invention

The present invention relates to an ultrasonic probe which is configured to transmit longitudinal vibration parallel to a longitudinal axis as a result of transmittance of ultrasonic vibration, and a manufacturing method of the ultrasonic probe.

2. Description of the Related Art

For example, WO2010/047395A1 discloses a treatment device with a treatment section located at a distal end portion of an ultrasonic probe and shaped like a hook. The treatment device generates ultrasonic vibration with the treatment section hooked to a biological tissue. Pulling the treatment section toward an operator allows the biological tissue to be treated.

The treatment device keeps the whole probe in balance based on the shape of the treatment section. Specifically, according to WO2010/047395A1, a distal end hook section is formed on an upper surface side of the treatment section disposed at the distal end of a probe main body section, and a recess portion is formed on a lower surface side of the treatment section. The treatment section is appropriately formed as described above so that the center of gravity of the treatment section coincides with the center of gravity of the probe main body section, thus stabilizing vibration.

BRIEF SUMMARY OF THE INVENTION

One aspect of an ultrasonic probe configured to transmit ultrasonic vibration along a longitudinal axis defined by a proximal end and a distal end thereof from the proximal end toward the distal end, according to the present invention includes: a first area including a proximal end portion, a distal end portion and a center axis which is defined by the proximal end portion and the distal end portion and which is parallel to the longitudinal axis, the first area having an antinode position of the ultrasonic vibration at the distal end portion, wherein a maximum distance from the center axis to an outer peripheral surface of the ultrasonic probe in a radial direction orthogonal to the center axis is a first distance; a treatment section located on a distal end side with respect to the distal end portion of the first area and having a center of gravity at a position displaced from the center axis of the first area; and a second area located between the first area and the treatment section so as to be continuous with the distal end portion of the first area and configured to have a gravity center axis positioned parallel to the center axis of the first area so as to pass through the center of gravity of the treatment section or be closer to the center of gravity than the center axis, wherein a maximum distance from the center axis to the outer peripheral surface of the ultrasonic probe in the radial direction orthogonal to the center axis is a second distance equal to or shorter than the first distance.

Another aspect of a manufacturing method of an ultrasonic probe with a proximal end and a distal end, according to the present invention includes: producing a first area adjacent to the proximal end of the ultrasonic probe to define a center axis of the first area, while leaving a site of a preparation body corresponding to a treatment section of the ultrasonic probe unprocessed, out of the preparation body that is long along a longitudinal axis defined by the proximal end and the distal end; machining the site corresponding to the treatment section and located at a distal end of the ultrasonic probe to define a center of gravity of the treatment section located at the distal end of the ultrasonic probe, at a position displaced from the center axis of the first area; and machining a second area between the first area and the treatment section in such a manner that a center of gravity of the second area is positioned parallel to the center axis of the first area so as to pass through the center of gravity of the treatment section.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing an ultrasonic treatment system according to an embodiment of the present invention;

FIG. 3A is a schematic diagram showing an ultrasonic probe of the ultrasonic probe unit of the ultrasonic treatment system according to the embodiment of the present invention;

FIG. 3C is a schematic diagram showing a variation of the ultrasonic probe of the ultrasonic probe unit of the ultrasonic treatment system according to the embodiment of the present invention;

FIG. 4D is a schematic diagram showing that a site of the preparation body shown in FIG. 4C and corresponding to the treatment area is machined to form a hook-shaped treatment area;

FIG. 4E is a schematic diagram showing that a site of the preparation body shown in FIG. 4D and corresponding to the second area is machined and partly removed to form the second area;

FIG. 5A is a schematic diagram showing a preparation body used to produce the ultrasonic probe of the ultrasonic probe unit of the ultrasonic treatment system according to the embodiment of the present invention;

FIG. 5B is a schematic diagram showing that, in production of the ultrasonic probe of the ultrasonic probe unit of the ultrasonic treatment system according to the embodiment of the present invention, a site of the preparation body shown in FIG. 5A which corresponds to the first area and the second area of the probe main body section is machined to form the first area, and a site of the preparation body corresponding to the treatment area is left unprocessed;

FIG. 5C is a schematic diagram showing that, in production of the ultrasonic probe of the ultrasonic probe unit of the ultrasonic treatment system according to the embodiment of the present invention, a site of the preparation body shown in FIG. 5B and corresponding to the second area of the probe main body section is machined, and a site of the preparation body shown in FIG. 5B and corresponding to the treatment area is left unprocessed;

FIG. 5D is a schematic diagram showing that a site of the preparation body shown in FIG. 5C and corresponding to the second area is machined to form the second area;

DETAILED DESCRIPTION OF THE INVENTION

Figure 2:
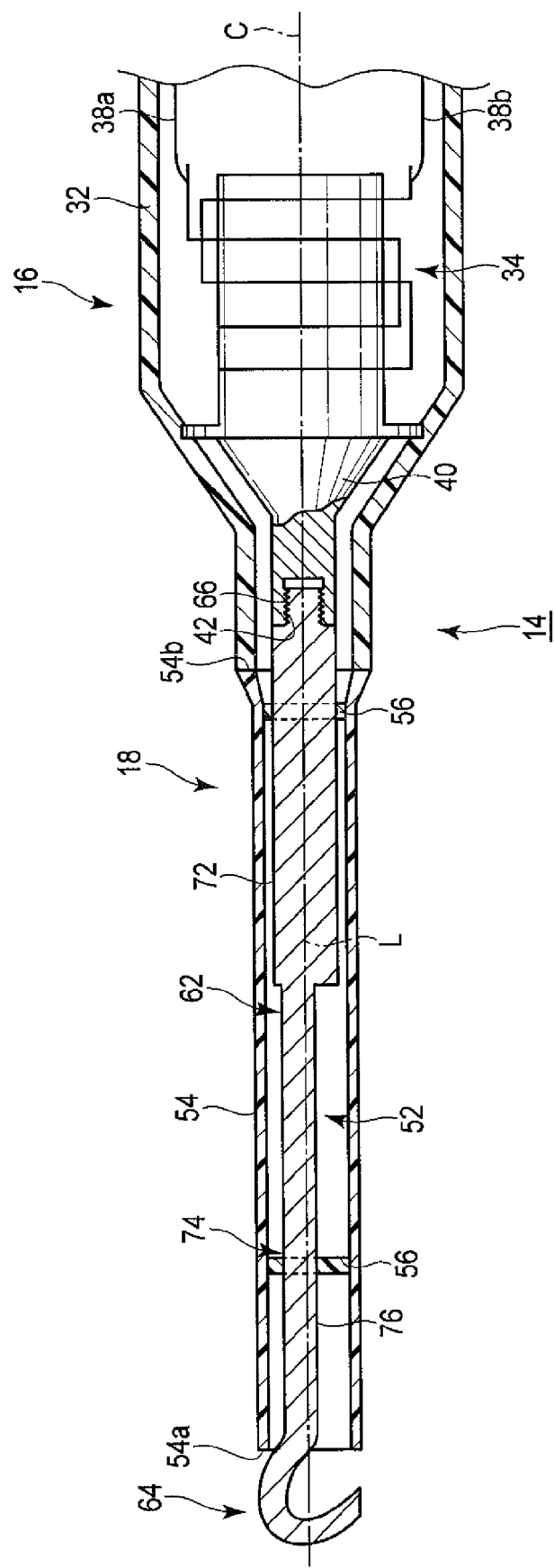
FIG. 2 is a schematic vertical cross-sectional view showing a part of an ultrasonic vibration generating unit and an ultrasonic probe unit of the ultrasonic treatment system according to the embodiment of the present invention.

An embodiment of the present invention including variations thereof will be described with reference to FIGS. 1 to 9B.

As shown in FIG. 1, an ultrasonic treatment system 10 includes a power supply unit 12 and an ultrasonic treatment unit 14 serving as an ultrasonic treatment device. The ultrasonic treatment unit 14 includes an ultrasonic vibration generating unit 16 and an ultrasonic probe unit 18.

The power supply unit 12 includes an electrical current supply section 22 that supplies electrical current to the ultrasonic vibration generating unit 16 and an input section 24. The input section 24 is connected to, for example, a foot switch (not shown in the drawings) to enable switching between a state where the electrical current supply section 22 supplies electrical current and a state where the supply of electrical current is stopped. Furthermore, an ultrasonic transducer 34 described below can be vibrated at an appropriate amplitude based on an operational state of the foot switch.

As shown in FIG. 2, the ultrasonic vibration generating unit 16 includes a transducer case 32 serving as an outer shell, an ultrasonic transducer 34 located inside the transducer case 32 and serving as a vibration generating unit, and a cable 36 extending from a proximal end of the transducer case 32 and detachably connected to the power supply unit 12. The transducer case 32 is formed of, for example, an insulating resin material.

The ultrasonic transducer 34 is, for example, of a BLT type. Electric wires 38a and 38b are connected to the ultrasonic transducer 34 at one end of each electric wire. The electric wires 38a and 38b pass through the cable 36 and are connected to the electrical current supply section 22 of the power supply unit 12 at the other end of each electric wire. The electrical current supply section 22 supplies electrical current to the ultrasonic transducer 34 via the electric wires 38a and 38b in the cable 36. Thus, the ultrasonic transducer 34 generates ultrasonic vibration. A horn 40 is coupled to a distal end direction side of the ultrasonic transducer 34 to increase the amplitude of ultrasonic vibration. The horn 40 is attached to, for example, the transducer case 32. Furthermore, an internal thread portion 42 is formed at a distal end portion of the horn 40.

As shown in FIG. 2, the ultrasonic probe unit 18 includes an ultrasonic probe 52 and a sheath 54. The sheath 54 is formed of an electrically insulating resin material or the like. The sheath 54 is formed to cover the entire outer peripheral surface of a first area 72 and a second area 74 of the ultrasonic probe 52, both of which will be described below, and to expose a treatment area 64 from a distal end 54a of the sheath 54. A proximal end 54b of the sheath 54 is detachably fixed to the transducer case 32. Furthermore, a ring 56 formed of, for example, a rubber material having insulating properties, is disposed between the ultrasonic probe 52 and the sheath 54 at a vibration node position. This enables an outer peripheral surface of the ultrasonic probe 52 to be separated from an inner peripheral surface of the sheath 52. If the ultrasonic probe 52 has a plurality of vibration node positions, the ring 56 is preferably disposed at each of the vibration node positions. For example, an annular recess portion is also preferably formed at the position where the ring 56 is disposed (vibration node position).

The sheath 54 and the ring 56 according to the embodiment may be unwanted depending on a usage state of the ultrasonic treatment unit 14.

The ultrasonic probe 52 shown in FIG. 3A is formed of, for example, a titanium alloy. The ultrasonic probe 52 includes a probe main body section 62 and a treatment area (treatment section) 64 provided closer to a distal end of the ultrasonic probe 52 than the probe main body section 62 to treat a biological tissue.

The probe main body section 62 includes an external thread portion 66 on an outer peripheral portion of a proximal end of the probe main body section 62. The external thread portion 66 engages, in a threaded manner, with the internal thread portion 42 formed on the horn 40 as shown in FIG. 2. Thus, the ultrasonic probe 52 is attached to the ultrasonic vibration generating unit 16. The ultrasonic probe 52 attached to the ultrasonic vibration generating unit 16 allows ultrasonic vibration generated by the ultrasonic transducer 34 to be transmitted to the ultrasonic probe 52. The ultrasonic vibration transmitted to the ultrasonic probe 52 enables the ultrasonic probe 52 to generate longitudinal vibration that is parallel to a center axis C in the direction of vibration and in the direction of transmission.

As shown in FIG. 3A, the probe main body section 62 extends in a longitudinal direction along the center axis C. The probe main body section 62 includes the first area 72 located on a proximal end side of the probe main body section 62 in a longitudinal direction thereof and including the external thread portion 66 formed at a most proximal end and the second area 74 provided on a distal end direction side of the first region 72. Preferably, the first area 72 is formed to be straight, and all transverse sections are the same in size and shape. Furthermore, the second area 74 is preferably formed to be straight, and all transverse sections are the same in size and shape. The second area 74 includes a treatment area 64 on a distal end direction side of the second region 74. For example, both the first area 72 and the second area 74 may be tapered so that transverse sections on the proximal end side are formed to be larger than cross sections on the distal end side.

According to the embodiment, the first area 72 shown in FIG. 3A and FIG. 3S is formed to be, for example, cylindrical. Thus, in the first area 72, the center axis C coincides with the center of gravity (gravity center axis) at the position of each transverse section orthogonal to the center axis C. That is, at any position between the distal end and the proximal end of the first area 72, the center axis C coincides with the center of gravity on a transverse section orthogonal to the center axis C. In other words, the center of gravity on each circular transverse section orthogonal to the longitudinal direction of the first area 72 corresponds to the center of the transverse section. Thus, the center axis C is defined by a set of centers of gravity on the respective cross sections between a distal end portion 73a and a proximal end portion 73b of the first area 72.

A boundary between the first area 72 and the second area 74, that is, the distal end portion 73a of the first area 72 and a proximal end portion 75b of the second area 74, is adjusted to correspond to an antinode position of vibration. For example, when a drive frequency is 47 kHz and the ultrasonic probe 52 is formed of 6-4Ti and has an outer diameter of approximately 6 mm, a half-wavelength is approximately 51 mm to approximately 52 mm. Thus, when the ultrasonic vibration generating unit 16 and the ultrasonic probe 52 are joined together at the antinode of the vibration, the length from a distal end of the ultrasonic transducer 34 (a proximal end of the horn 40) to the distal end portion 73a of the first area 72 of the probe main body section 62 is 51 mm to 52 mm×n (n: an integer of one or larger). In other words, the length from the distal end of the ultrasonic transducer 34 (the proximal end of the horn 40) to the distal end portion 73a of the first area 72 of the probe main body section 62 is an integral multiple of the half-wavelength (n times as large as the half-wavelength). The total length of the second area 74 and the treatment area 64 is preferably an integral multiple of the half-wavelength (n times as large as the half-wavelength).

When the ultrasonic transducer 34 has a resonant frequency of 23.5 kHz, the half-wavelength is approximately 102 mm to approximately 104 mm. In this case, the length from the distal end of the ultrasonic transducer 34 (the proximal end of the horn 40) to the distal end portion 73a of the first area 72 of the probe main body section 62 is an integral multiple of, for example, 102 mm to 104 mm. Furthermore, the total length of the second area 74 and the treatment area 64 is an integral multiple of, for example, 102 mm to 104 mm.

Figure 3B:
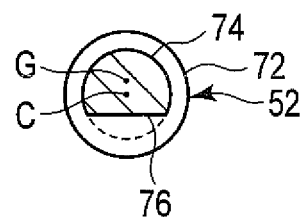
FIG. 3B is a schematic horizontal cross-sectional view of the ultrasonic probe of the ultrasonic probe unit of the ultrasonic treatment system according to the embodiment of the present invention, the cross-sectional view being taken along line 3B-3B in FIG. 3A.

The treatment region 64 shown in FIG. 3A is bent relative to the distal end portion 75a of the second area 74 of the probe main body section 62. In the embodiment, the treatment area 64 is shaped like a hook. In the treatment area 64, the center of gravity is displaced to a position shown by reference symbol G0 in FIG. 3A relative to the center axis C of the first area 72. In particular, the center of gravity G0 of the treatment area 64 in FIG. 3A is displaced toward an upper side of FIG. 3A and FIG. 3B relative to the center axis C.

A set of centers of gravity on transverse sections in the second area 74 which are orthogonal to the center axis C of the first area 72 is linear as shown by reference symbol G in FIG. 3A and FIG. 3B. The straight line shown by reference symbol G is parallel to the center axis C of the first area 72, but is not the same as and is positioned differently from the center axis C. For example, when the treatment area 64 is formed as shown in FIG. 3A and the center of gravity G0 of the treatment area 64 is displaced upward from the center axis C in FIG. 3A and FIG. 3B, the second area 74 is formed by machining such that the straight line G, a set of centers of gravity on transverse sections orthogonal to the center axis C of the first area 72, passes through the barycenter G0 of the treatment area 64, or closer to the center of gravity G0 than the center axis C. That is, the straight line G (center axis) passing through the center of gravity of the second area 74 is parallel to the center axis C, passing through the center of gravity of the first area, and is not the same as and is positioned differently from the center axis C. In other words, the center axis of the second area (straight line G) is parallel to the center axis C of the first area and passes through the center of gravity G0, or closer to the center of gravity G0 than the center axis C.

The center of gravity G is isolated at the boundary between the first area 72 and the second area 74, and the boundary position corresponds to the antinode position of the vibration. The antinode position of the vibration is displaced more significantly than the other positions. However, the state of a medium near the antinode position of the vibration remains unchanged, resulting in no stress, as is the case where no wave is generated. Thus, even when the center of gravity is displaced at the antinode position of the vibration, no or substantially no adverse effect is exerted on the vibration. Furthermore, both in the first area 72 and in the second area 74, the center of gravity lies on a straight line parallel to the center axis C and is constant over every half-wavelength. This allows longitudinal vibration to be stabilized.

A procedure for manufacturing (method for manufacturing) the ultrasonic probe 52 will be described with reference to FIG. 4A to FIG. 4E. In this case, an example will be described in which the treatment area 64 is shaped like a hook as shown in FIG. 3A.

Figure 4A:
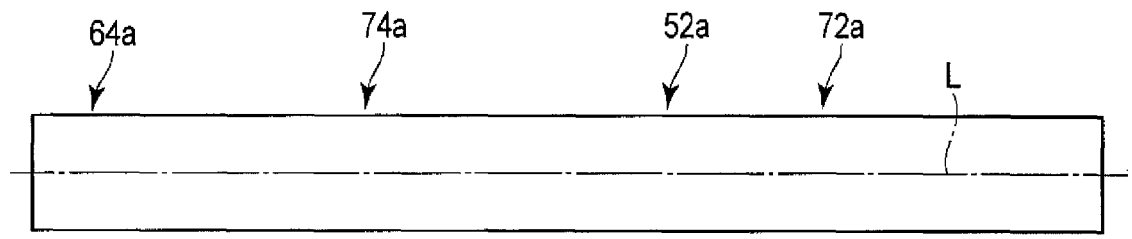
FIG. 4A is a schematic diagram showing a preparation body used to produce the ultrasonic probe of the ultrasonic probe unit of the ultrasonic treatment system according to the embodiment of the present invention.

First, as shown in FIG. 4A, a rod-like member (preparation body) is prepared which is formed of, for example, a titanium alloy material (preparation body) 52a and which is long and straight along a longitudinal direction (longitudinal axis) L. An outer peripheral surface of a transverse section orthogonal to the longitudinal direction of the rod-like member 52a may be, for example, circular or polygonal. The length of the rod-like member 52a is determined by the resonant frequency of the ultrasonic transducer 34 used, the length of the connected horn 40, a target biological tissue to be treated, and the like.

When the outer peripheral surface of a transverse section of the rod-like member 52a is not circular, the outer peripheral surface of the rod-like member 52a is preferably machined to be circular using a lathe or the like. The maximum outer diameter of the rod-like member 52a is appropriately determined based on, for example, the inner diameter (for example, 5 mm, 10 mm, 12 mm, or the like) of a trocar inserted into a body cavity, though the maximum outer diameter depends on whether or not the sheath 54 is arranged on the outer periphery of the ultrasonic probe 52 and the thickness of the sheath 54.

Figure 4B:
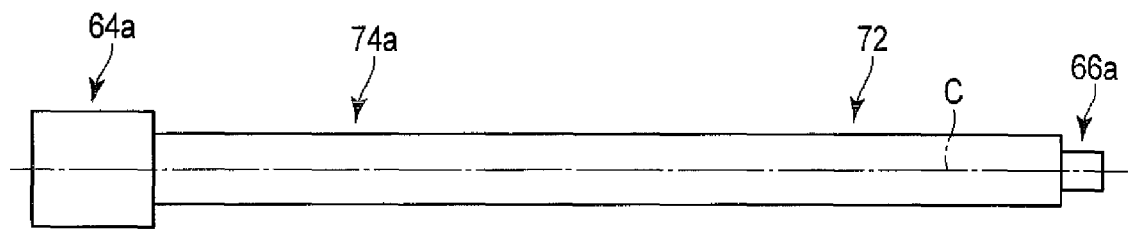
FIG. 4B is a schematic diagram showing that, in production of the ultrasonic probe of the ultrasonic probe unit of the ultrasonic treatment system according to the embodiment of the present invention, a site of the preparation body shown in FIG. 4A which corresponds to a first area and a second area of the probe main body section is machined to form the first area, and a site of the preparation body corresponding to a treatment area is left unprocessed.

The rod-like member 52a shown in FIG. 4A is placed on a lathe, and the outer peripheral surface of a site 72a of the first area 72 is machined so as to be shaped like the first area 72 as shown in FIG. 4B. At this time, the outer peripheral surface of a site 74a corresponding to the second area 74 is also preferably machined so as to have an outer diameter similar to the outer diameter of the first area 72. Furthermore, a cylindrical portion 64a forming the treatment area 64 is left on a distal end direction side of the site 74a corresponding to the second area 74. At this stage, the first area 72 is formed.

A site 66a corresponding to the external thread portion 66 may be formed at this stage or after the treatment area 64 and the second area 74 are formed. Alternatively, the site 66a corresponding to the external thread portion 66 may be formed before the first area 72 is formed. Threads may subsequently be formed in the site 66a corresponding to the external thread portion 66 at any stage.

Figure 4C:
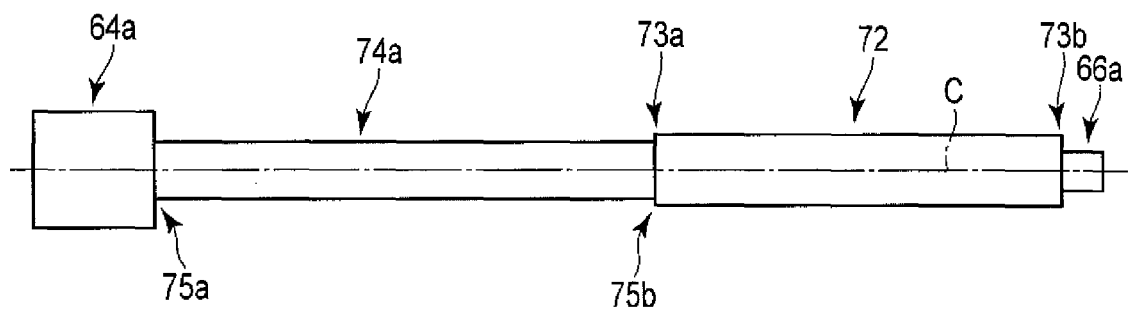
FIG. 4C is a schematic diagram showing that, in production of the ultrasonic probe of the ultrasonic probe unit of the ultrasonic treatment system according to the embodiment of the present invention, a site of the preparation body shown in FIG. 4B and corresponding to the second area of the probe main body section is machined, and a site of the preparation body shown in FIG. 4B and corresponding to the treatment area is left unprocessed.

Then, as shown in FIG. 4C, the outer peripheral surface of the site 74a corresponding to the second area 74 is further machined so as to have a smaller outer diameter than the first area 72. At this time, the center of gravity on the first area 72 and the center of gravity on the site 74a corresponding to the second area 74 both still lie on the same center axis C of the first area 72.

Then, as shown in FIG. 4D, the site 64a corresponding to the treatment area 64 is appropriately machined using, for example, a five-axis NC lathe or forging, to produce a treatment area 64. When, for example, an ultrasonic probe 52 used in a trocar with an inner diameter of 5 mm is produced, the treatment area 64 is formed such that the range of the treatment area 64 relative to the center axis C does not exceed 2.5 mm. In other words, the treatment area 64 is formed such that an upper side of the treatment area 64 relative to the center axis C in FIG. 4D is smaller than 2.5 mm, and a lower side of the treatment area 64 relative to the center axis C in FIG. 4D is smaller than 2.5 mm so as to permit insertion into a trocar with an inner diameter of 5 mm. The thus-determined shape of the treatment area 64 determines the center of gravity G0 of the treatment area 64. In this case, the center of gravity G0 of the treatment area 64 lies above the center axis C in FIG. 4D. The center of gravity of the site 74a corresponding to the second area 74 lies on the same center axis C of the first area 72. Thus, the center of gravity G0 of the treatment area 64 is displaced from the center of gravity of the site 74a corresponding to the second area 74.

As shown in FIG. 4E, the site 74a corresponding to the second area 74 is partly removed using, for example, a milling machine so that an imaginary straight line G passing and through the center of gravity G0 and parallel to the center axis C of the treatment area 64 provide a set of centers of gravity in the second area 74. In the embodiment, the lower portion in FIG. 4D is partly removed flat to form a flat surface 76 shown in FIG. 3A, FIG. 3B, and FIG. 4E. That is, the barycenter G of the second area 74 is displaced upward, in FIG. 4E, relative to the center of gravity of the site 74a corresponding to the second area 74.

For example, when the treatment area 64 shown in FIG. 4D and shaped like a hook or the like is formed, the barycenter G0 of the treatment area 64 is consequently defined displaced from the center axis C of the first area 72. Thus, as shown in FIG. 4E, the second area 74 is machined from the distal end to the proximal end thereof so that the center of gravity of the second area 74 is positioned parallel to the center axis C so as to pass through the center of gravity G0 of the treatment area 64 or closer to the center of gravity G0 than the center axis C.

As described above, the ultrasonic probe 52 can be produced such that the center of gravity (gravity center axis) G between the distal end and proximal end of the second area 74 is displaced parallel to the center axis C so as to coincide with the center of gravity G0 of the treatment area 64 or to be closer to the center of gravity G0 than the center axis C.

Figure 5E:
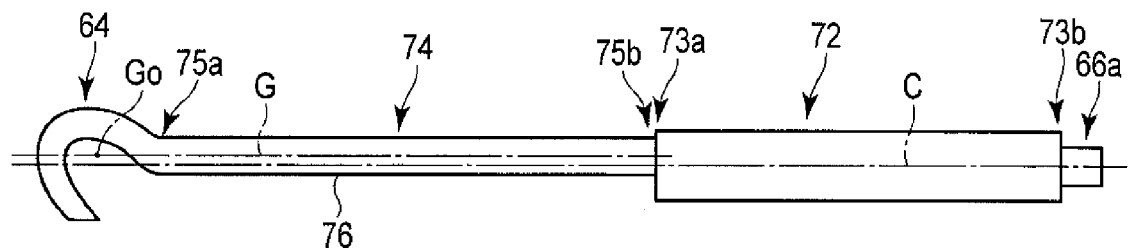
FIG. 5E is a schematic diagram showing that a site of the preparation body shown in FIG. 5D and corresponding to the treatment area is machined to form a hook-shaped treatment area.

In this case, the example has been described in which the formation of the treatment area 64 is followed by the machining of the second area 74. However, the machining of the second area 74 may of course be followed by the formation of the treatment area 64. This will be described in brief using FIGS. 5A to 5E. FIG. 5A corresponds to FIG. 4A, FIG. 5B corresponds to FIG. 4B, and FIG. 5C corresponds to FIG. 4C. Thus, description of FIGS. 5A to 5C is omitted.

As shown in FIG. 5D, unlike in FIG. 4D, the second area 74 is formed before the formation of the treatment area 64 based on machining, and the gravity center axis G of the second area 74 is defined at a position displaced from the center axis C of the first area 72. This is because the center of gravity G0 can be easily determined after the treatment area 64 is machined based on, for example, experience in forming a large number of ultrasonic probes 52 with the same shape and design.

Then, as shown in FIG. 5E, unlike in FIG. 4E, the second area 74 is formed, and the treatment area 64 is formed by machining to have a predetermined shape (a shape specified by design). At this time, the treatment area 64 can be formed so that the center of gravity G of the second area 74 passes through the center of gravity G0 of the treatment area 64, or be closer to the center of gravity G0 than the center axis C.

Effects will be described in brief which are exerted using the ultrasonic treatment system 10 shown in FIG. 1 and, for example, including the ultrasonic probe 52 produced in steps described with reference to FIGS. 4A to 4E or FIGS. 5A to 5E.

The external thread portion 66 at the proximal end of the ultrasonic probe 52 is engaged with the internal thread portion 42 of the horn 40 in a threaded manner.

A trocar (not shown in the drawings) is pierced into, for example, the abdominal cavity and fixed. In this state, the treatment area 64 of the ultrasonic probe unit 18 is guided, via the trocar, through the body cavity toward the biological tissue to be treated. For example, with the treatment area 64 shaped like a hook hooked to the biological tissue, the foot switch (not shown in the drawings) is operated to transmit a signal to the electrical current supply section 22 via the input section 24 to switch to the state where the electrical current supply section 22 supplies electrical current. Thus, the ultrasonic transducer 34 vibrates to transmit vibration to the ultrasonic probe 52 via the horn 40. That is, the ultrasonic probe 52 transmits longitudinal vibration resulting from ultrasonic vibration from the proximal end toward the distal end of the ultrasonic probe 52 along the longitudinal axis L defined by the proximal end and distal end.

At this time, the center axis (center of gravity) C is straight from the proximal end of the horn 40 to the distal end portion 73a of the first area 72 of the ultrasonic probe 52 and is not displaced. Thus, the longitudinal vibration from the ultrasonic transducer 34 is stably transmitted through the horn 40 to the distal end portion 73a of the first area 72 without vibration loss.

The center of gravity in the first area 72 and the center of gravity in the second area 74 are shifted from each other at the boundary between the distal end portion 73a of the first area 72 and the proximal end portion 75b of the second area 74. However, the boundary corresponds to the antinode position of the vibration and thus does not affect the vibration. The gravity center axis G is straight from the proximal end portion 75b to the distal end portion 75a of the second area 74 and is not displaced. Thus, the longitudinal vibration from the ultrasonic transducer 34 is stably transmitted through the horn 40 and the first area 72 to the distal end portion 75a of the second area 74 without vibration loss. The center of gravity G0 of the treatment area 64 lies on an axis corresponding to an extension of the barycenter axis G of the second area 74. Consequently, the longitudinal vibration from the ultrasonic transducer 34 is stably transmitted through the horn 40, the first area 72, and the second area 74 to the distal end of the treatment area 64 without vibration loss.

Therefore, the ultrasonic vibration can be transmitted to the hooked biological tissue through the treatment area 64 with vibration loss minimized. Thus, pulling the treatment area 64 toward the operator allows the biological tissue to be appropriately treated, for example, incised.

Figure 6A:
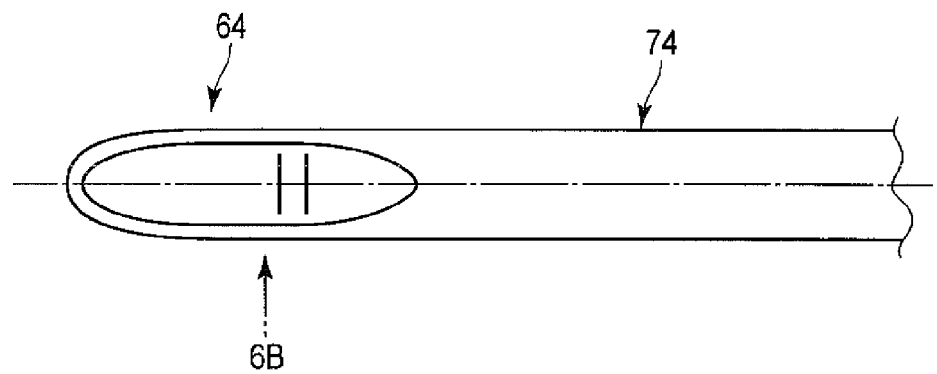
FIG. 6A is a schematic top view showing a spatula-shaped treatment area in a variation of the ultrasonic probe of the ultrasonic probe unit of the ultrasonic treatment system according to the embodiment of the present invention, as seen in a direction shown by arrow 6A in FIG. 6B.
Figure 6B:
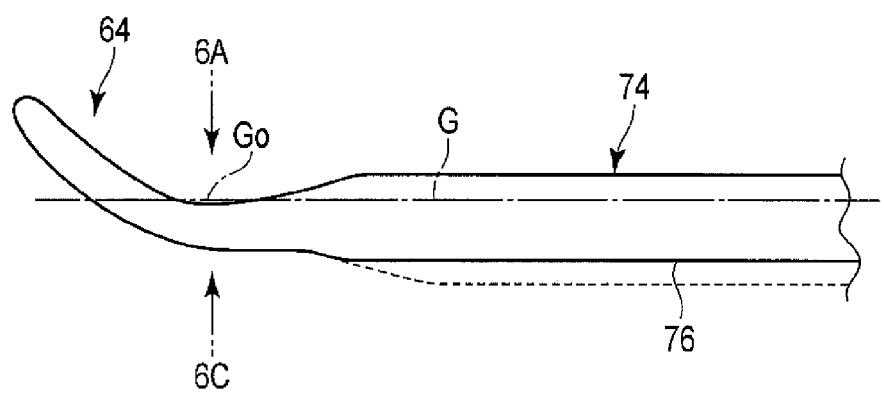
FIG. 6B is a schematic side view showing the spatula-shaped treatment area in the variation of the ultrasonic probe of the ultrasonic probe unit of the ultrasonic treatment system according to the embodiment of the present invention, as seen in a direction shown by arrow 6B in FIG. 6A and by arrow 6B in FIG. 6C.
Figure 6C:
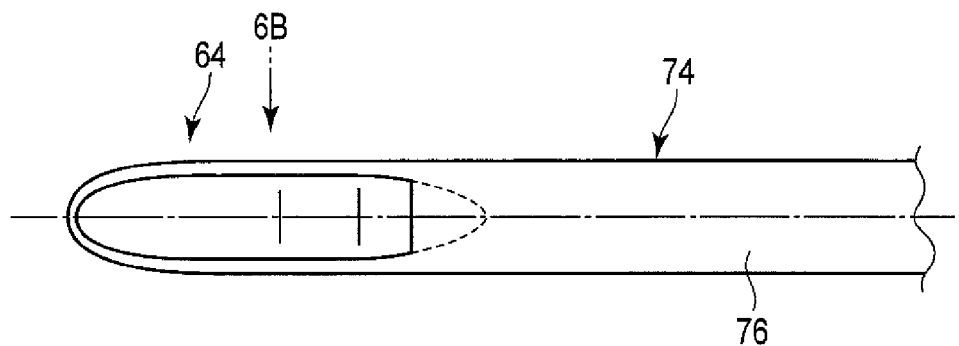
FIG. 6C is a schematic top view showing the spatula-shaped treatment area in the variation of the ultrasonic probe of the ultrasonic probe unit of the ultrasonic treatment system according to the embodiment of the present invention, as seen in a direction shown by arrow 6C in FIG. 6B.
Figure 7:
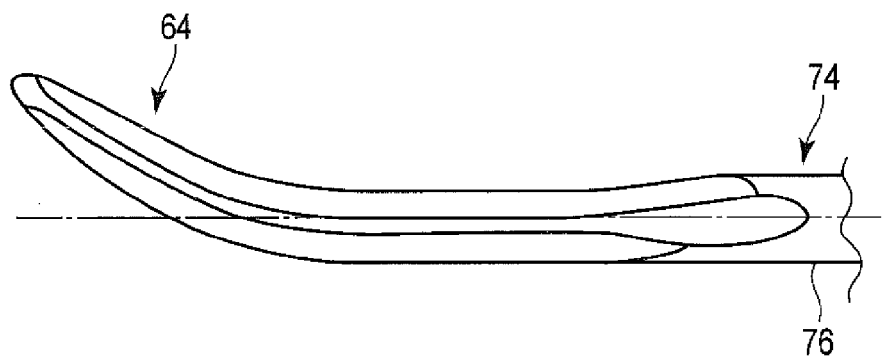
FIG. 7 is a schematic side view showing a scissors-shaped treatment area in a variation of the ultrasonic probe of the ultrasonic probe unit of the ultrasonic treatment system according to the embodiment of the present invention.
Figure 8A:
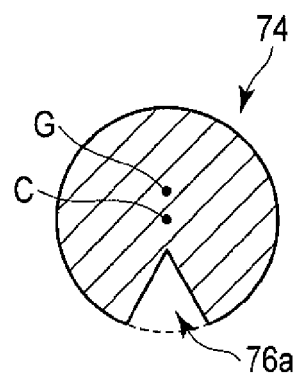
FIG. 8A is a schematic horizontal cross-sectional view showing a second area of a variation of the ultrasonic probe of the ultrasonic probe unit of the ultrasonic treatment system according to the embodiment of the present invention.
Figure 8B:
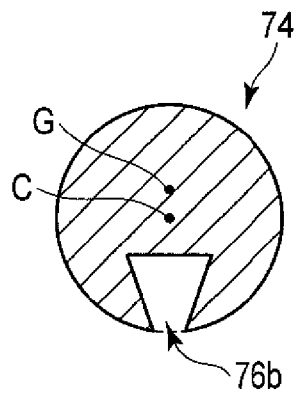
FIG. 8B is a schematic horizontal cross-sectional view showing a second area of a variation of the ultrasonic probe of the ultrasonic probe unit of the ultrasonic treatment system according to the embodiment of the present invention.
Figure 8C:
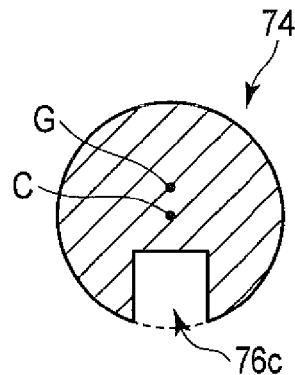
FIG. 8C is a schematic horizontal cross-sectional view showing a second area of a variation of the ultrasonic probe of the ultrasonic probe unit of the ultrasonic treatment system according to the embodiment of the present invention.
Figure 8D:
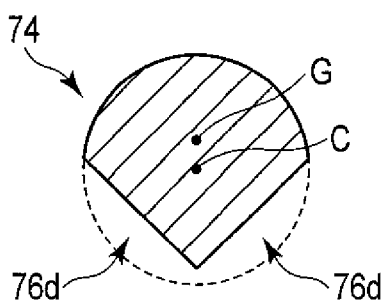
FIG. 8D is a schematic horizontal cross-sectional view showing a second area of a variation of the ultrasonic probe of the ultrasonic probe unit of the ultrasonic treatment system according to the embodiment of the present invention.
Figure 8E:
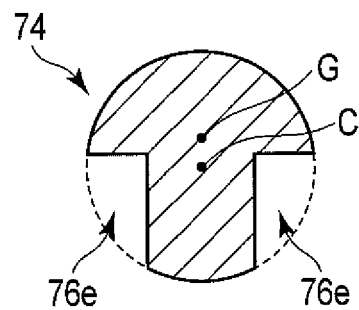
FIG. 8E is a schematic horizontal cross-sectional view showing a second area of a variation of the ultrasonic probe of the ultrasonic probe unit of the ultrasonic treatment system according to the embodiment of the present invention.
Figure 8F:
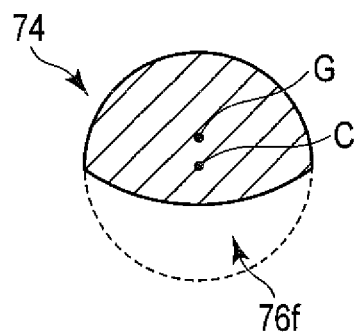
FIG. 8F is a schematic horizontal cross-sectional view showing a second area of a variation of the ultrasonic probe of the ultrasonic probe unit of the ultrasonic treatment system according to the embodiment of the present invention.

When the treatment region 64 is appropriately shaped, the center of gravity of the second area 74 may be correspondingly adjusted. This ensures an appropriate degree of freedom for the shape of the treatment area 64. For example, the treatment area 64 is not limited to the hook shape shown in FIG. 3A, but the treatment area 64 shaped like a paddle as shown in FIGS. 6A to 6C, or like scissors as shown in FIG. 7, may be suitably used. The center of gravity of the second area 74 is adjusted such that the center of gravity G defined by a set of centers of gravity on transverse sections in the second area 74 orthogonal to the center axis C of the first area 72 coincides with the center of gravity G0 of the treatment area 64, or is closer to the center of gravity G0 than the center axis C. Thus, stable longitudinal vibration can be transmitted to the first area 72, to the second area 74, and further to the treatment area 64.

In the ultrasonic probe 52 according to the embodiment, the longitudinal vibration can be prevented from being disturbed, or be made difficult to disturb, by setting the center of gravity of the ultrasonic probe 52 to be straight over a half-wavelength portion or an integral multiple thereof on the distal end side of the ultrasonic probe 52. In the ultrasonic probe 52 according to the embodiment, since the boundary between the first area 72 and the second area 74 corresponds to the antinode position of the vibration, the center of gravity of the first area 72 and the center of gravity of the second area 74 are displaced from each other at the boundary between the first area 72 and the second area 74, the center of gravity of the first area 72 lies on the center axis C, and the center of gravity in the second area 74 and the treatment area 64 lies on the straight line G which is parallel to the center axis C, the longitudinal vibration from the ultrasonic transducer 34 can be stably transmitted to the treatment area 64 via the ultrasonic probe 52. That is, since the longitudinal vibration can be made difficult to disturb simply by adjusting the center of gravity over a half-wavelength portion or an integral multiple thereof on the distal end side of the ultrasonic probe 52, undesirable vibration such as a transversal wave can be prevented from being generated, particularly in the probe main body section 62 of the ultrasonic probe 52, without an increase in machining costs.

Furthermore, in the above-described procedure of manufacturing the ultrasonic probe 52, the step has been described in which the site 74a corresponding to the second area 74 is formed to have an outer diameter smaller than the outer diameter of the first area 72 as shown in FIG. 4C and FIG. 5C. However, this step may be omitted. That is, if the gravity center axis G can be displaced relative to the center axis C by machining the site 74a corresponding to the second area 74 to form, for example, the flat surface 76 as shown in FIG. 3C, then the diameter of the site 74a need not necessarily be reduced. Instead, the second area 74 may be formed to have a larger diameter.

For example, the second area 74 may be formed like a cylinder with a center axis displaced from the center axis C of the cylindrical first area 72 (that is, the second area 74 is made eccentric to the first area 72). That is, the second area 74 can also be formed to be cylindrical. However, the formation of the cylindrical second area 74 with a center of gravity displaced from the center of gravity of the first area 72 incurs higher machining costs than the formation in the example shown in FIGS. 4A to 4E or FIGS. 5A to 5E described above.

Thus, it is advantageous in terms of costs to set both the cylindrical first and second areas 72 and 74 to have the same center axis and then to adjust the center of gravity of the second area 74 by machining one surface (for example, a flat surface 76) of the second area 74.

In this case, in addition to cutting a part of the cylinder so that the second area 74 has the flat surface 76 shown in FIG. 3B, shaping the second area 74 as shown in FIGS. 8A to 8F is also suitable. Any of various well-known machine tools may be used to machine the second area 74 as shown in FIGS. 8A to 8F. Machined portions (removed surfaces) 76a, 76b, 76c, 76d, 76e, and 76f removed as shown in FIGS. 8A to 8F allow the center of gravity G to be displaced upward relative to the center C of an imaginary circle in each of the figures. That is, in the second area 74, the barycenter G can be displaced by forming an odd-shaped portion which is not circular and which fails to exhibit point symmetry with respect to the center axis C of the first area 72, for example, as shown by reference numerals 76, 76a, 76b, 76c, 76d, 76e, and 76f. Even in such cases as shown by reference numerals 76, 76a, 76b, 76c, 76d, and 76e, the ultrasonic probe 52 can be formed more inexpensively than in the case where the shape of the second area 74 is kept cylindrical.

The first area 72 of the above-described ultrasonic probe 52 is formed to exhibit point symmetry with respect to the center axis C of the first area 72. The second area 74 is formed to exhibit asymmetry with respect to the gravity center axis G so that the gravity center axis G passes through the center of gravity G0 of the treatment area 64.

In the embodiment, the case has been described in which the outer peripheral surface of the first area 72 is circular, whereas the outer peripheral surface of the second area 74 is partly shaped like a part of a circle. Also, the first area is preferably shaped like a polygon with 2n sides (n: a natural number) such as a hexagon as shown by reference numeral 172 in FIG. 9A or like a polygon with 2n+1 sides (n: a natural number) such as a pentagon as shown by reference numeral 272 in FIG. 9B. Furthermore, a machined portion (in this case, the flat surface 76) is preferably formed in the second area as shown by reference numeral 174 in FIG. 9A by machining and removing a part of a hexagon. Similarly, a machined portion (in this case, the flat surface 76) is preferably formed in the second area as shown by reference numeral 274 in FIG. 9B by machining and removing a part of a pentagon.

Figure 9A:
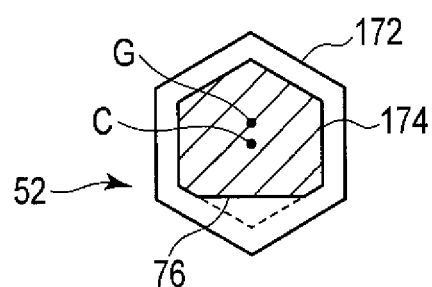
FIG. 9A is a schematic horizontal cross-sectional view showing a variation of the ultrasonic probe of the ultrasonic probe unit of the ultrasonic treatment system according to the embodiment of the present invention in which the first area of the probe main body section is shaped like a regular hexagon, and in which the second area is formed by machining and partly removing the regular hexagon so that the center of gravity of the second area is displaced from the center of gravity of the first area.
Figure 9B:
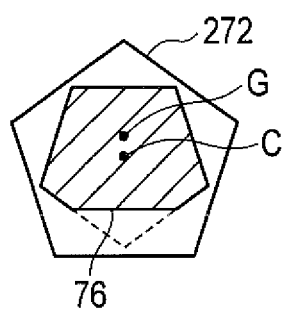
FIG. 9B is a schematic horizontal cross-sectional view showing a variation of the ultrasonic probe of the ultrasonic probe unit of the ultrasonic treatment system according to the embodiment of the present invention in which the first area of the probe main body section is shaped like a regular pentagon, and in which the second area is formed by machining and partly removing the regular pentagon so that the center of gravity of the second area is displaced from the center of gravity of the first area.

When the first area is shaped like a regular pentagon as shown by 272 in FIG. 9B, the center of gravity of the first area 272, that is, the center axis C, lies at a position where a perpendicular line of a midpoint of one side (first side) extended to a vertex (first vertex) opposite to the first side intersects a perpendicular line of a midpoint of another side (second side) extended to a vertex (second vertex) opposite to the second side.

Furthermore, the first area and the second area are suitably formed by appropriately combining the hexagon shown in FIG. 9A with the pentagon shown in FIG. 9B. That is, the probe main body section 62 is suitably formed by, for example, shaping the first area 72 like a pentagon and shaping the second area 74 like a hexagon and removing and partly removed. Alternatively, the probe main body section 62 may be suitably formed by, for example, shaping the first area 72 like a hexagon and shaping the second area 74 like a pentagon and removing part of the shape by machining.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe configured to transmit an ultrasonic vibration along a longitudinal axis defined by a proximal end and a distal end thereof from the proximal end toward the distal end, wherein the proximal end is located on a distal end side of a horn which is configured to transmit the ultrasonic vibration along with the longitudinal axis, the ultrasonic probe comprising:
   a first area including a proximal end portion, a distal end portion and a center axis which is defined by the proximal end portion and the distal end portion and which is parallel to the longitudinal axis, the first area having an antinode position of the ultrasonic vibration at the distal end portion, wherein a maximum distance from the center axis to an outer peripheral surface of the ultrasonic probe in a radial direction orthogonal to the center axis is a first distance;
   a treatment section located on a distal end side with respect to the distal end portion of the first area and having a center of gravity at a position displaced from the center axis of the first area; and
   a second area located between the first area and the treatment section so as to be continuous with the distal end portion of the first area and configured to have a gravity center axis parallel to the center axis of the first area and from a position which passes through the center of gravity of the treatment section to a position which is closer to the center of gravity than the center axis, wherein a maximum distance from the center axis to the outer peripheral surface of the ultrasonic probe in the radial direction orthogonal to the center axis is a second distance equal to or shorter than the first distance.

2. The ultrasonic probe according to claim 1, wherein the gravity center axis of the second area is displaced from the center axis of the first area at the distal end portion of the first area.

3. The ultrasonic probe according to claim 1, wherein:
   the treatment section is bent with respect to a distal end portion of the second area in such a manner that the center of gravity of the treatment section is displaced from the center axis of the first area, and
   the gravity center axis of the second area is positioned, by removing a part of the second area, so as to pass through the center of gravity of the treatment section or close to the center of gravity of the treatment section with respect to the center axis of the first area.

4. The ultrasonic probe according to claim 1, wherein the treatment section is shaped like a hook or a spatula.

5. The ultrasonic probe according to claim 1, wherein, in the second area, a part of a cylinder is removed so as to define the center of gravity of the second area at a position displaced from the center axis.

6. The ultrasonic probe according to claim 1, wherein a transverse section orthogonal to the gravity center axis has an identical shape from the distal end portion of the first area to the distal end portion of the second area with which the treatment section is located in a continuous manner.

7. The ultrasonic probe according to claim 1, wherein an external shape of a transverse section in the second area orthogonal to the gravity center axis is an odd shape different from a circle.

8. The ultrasonic probe according to claim 1, wherein an external shape of a transverse section in the first area orthogonal to the center axis is a circle.

9. The ultrasonic probe according to claim 1, wherein the treatment section is shaped like a hook.

10. An ultrasonic treatment unit comprising:
   an ultrasonic probe according to claim 1; and
   an ultrasonic transducer disposed on a proximal end side of the ultrasonic probe and configured to input ultrasonic vibration to the ultrasonic probe.

11. The ultrasonic treatment unit according to claim 10, further comprising a horn provided between the ultrasonic probe and the ultrasonic transducer.

12. A manufacturing method of an ultrasonic probe with a longitudinal axis defined by a proximal end and a distal end, the method comprising:
   producing a first area adjacent to the proximal end of the ultrasonic probe and defining a center axis of the first area, while leaving a site of a preparation body corresponding to a treatment section of the ultrasonic probe unprocessed, out of the preparation body that is long along the longitudinal axis;
   machining the site located at the distal end as the treatment section of the ultrasonic probe to define a center of gravity of the treatment section, at a position displaced from the center axis of the first area; and
   machining a second area adjacent to the treatment section along with the longitudinal axis and between the first area and the treatment section in such a manner that a gravity center axis of the second area is positioned parallel to the center axis of the first area so as to pass through the center of gravity of the treatment section.

13. The manufacturing method according to claim 12, wherein the machining the second area comprises setting a maximum distance in a radial direction orthogonal to the center axis in the second area to be a second distance shorter than a first distance when the first distance is defined as a maximum distance in a radial direction orthogonal to the center axis in the first area.

14. A manufacturing method of an ultrasonic probe with a longitudinal axis defined by a proximal end and a distal end, the method comprising:
   producing a first area adjacent to the proximal end of the ultrasonic probe and defining a center axis of the first area, while leaving a site of a preparation body corresponding to a treatment section of the ultrasonic probe unprocessed, out of the preparation body that is long along the longitudinal axis;
   machining in such a manner that a gravity center axis of a second area continuous with a distal end side of the first area, is parallel to the center axis of the first area and at a position displaced from the center axis of the first area; and
   machining the site corresponding to the treatment section and which is continuous with a distal end side of the second area to form the treatment section into a predetermined shape, wherein the gravity center axis of the second area is between a position which passes through a center of gravity of the treatment section and a position which is closer to the center of gravity of the treatment section than the center axis of the first area.

15. The manufacturing method according to claim 14, wherein the machining the second area comprises setting a maximum distance in a radial direction orthogonal to the center axis in the second area to be a second distance shorter than a first distance when the first distance is defined as a maximum distance in a radial direction orthogonal to the center axis in the first area.

\* \* \* \* \*